United States Patent [19]

Mungia, Sr.

[11] Plant 5,049

[45] May 10, 1983

[54] ROSE PLANT

[76] Inventor: Fred A. Mungia, Sr., P.O. Box 338, McFarland, Calif. 93250

[21] Appl. No.: 320,720

[22] Filed: Nov. 12, 1981

[51] Int. Cl.[3] ..... A01H 5/00

[52] U.S. Cl. ..... Plt./2

[58] Field of Search ..... Plt./2

*Primary Examiner*—James R. Feyrer

[57] ABSTRACT

A new and distinct variety of rose, named 'Climbing Blue Moon' plant of the Climbing Hybrid Tea Class, a sport of the unpatented rose variety known as Blue Moon, characterized by a very vigorous growing bush producing excellent formed lilac blue flowers of good substance and size.

1 Drawing Figure

1

The present invention relates to a new and distinct variety of rose plant of the climbing hybrid tea class, which originated as a sport of the variety, "Blue Moon", (synonyms Mainzer Fastnacht, Sissi) nonpatented variety. The sport has been named "Climbing Blue Moon".

The new variety was discovered by me at my nursery in McFarland, Calif., in a cultivated area. My attention was drawn to a plant that was presumed to be the variety, "Blue Moon," but which exhibited definite climbing characteristics in that it produced canes which were 8 to 10 feet in length. This new variety has been asexually reproduced by budding, under my supervision at McFarland, Calif. Observations of the above asexual reproductions of the new variety have shown that the climbing habit comes true to form and is transmissible through succeeding asexual propagations.

This new variety is distinguished from its parent only by its climbing habit of growth and is classified as a climbing hybrid tea rose.

Among the novel characteristics possessed by this rose which distinguishes it from all other varieties of which I am aware are:

1. The plant is an everblooming climber and produces 4½–5 inch flowers that last well. Flowers appear one to a stem and in clusters at times on the same plant.
2. The plant is well branched, vigorous and free standing with upright spreading habit producing canes from 8 to 10 feet tall in length.
3. Flowers have a strong damask fragrance.
4. A general color tonality of the flowers corresponding to light violet or lilac lightly undercast with soft pinkish blend of lavendar tones, and the flowers are long lasting and unfading.
5. The plant is very hardy and disease resistant.

The accompanying drawing shows specimen plants of the new variety which is illustrative of the typical climbing habit of growth and flower color in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "84D" is plate 84D of The Royal Horticultural Society Colour Chart.

2

The following observations are made of specimns grown outdoors at Kern County, Calif., during the month of October.

FLOWER

Blooming habit: Continuous.

A. Bud:
- (1) *Size.*—Large.
- (1) *Form.*—Pointed.
- (3) *Color.*—When sepals first divide: near to RHS 100C with dark streaking where exposed to light. When petals begin to unfurl: near to but lighter then RHS 100C with dark violet overtones. When half blown: inside of petals — is near 95D with purple pink undertones of RHS 84D and RHS 69C color changes very little as flower opens. Reverse side of petal: substantially the same except for darker blue streaking in cool weather.
- (4) *Sepals.*—Short and pointed.
- (5) *Peduncle.*—Length 2½ to 3 inches. Aspect — smooth. Strength — heavy.
- *Color.*—RHS 138B with slight purple caste where exposed to light.

B. Bloom:
- (1) *Size.*—Average size when fully expanded: 4½–5 inches.
- (2) *Borne.*—Singly on long canes, and several together on short branching canes.
- (3) *Form.*—High centered with good recurl.
- (4) *Petalage.*—40.
- (5) *Color.*—During first two days. Center of flower — near RHS 95D. Inside of petals — RHS 94D blending to RHS 84C with RHS 69C undertones at edge of petals. Reverse of petals — near to RHS 100C with some streaking.
- (6) *Color change.*—General tonality from a distance — near RHS 84C with undertones of RHS 69C giving a soft pink caste to the flower. Color is very stable and uniform and retains good color until petals drop.

C. Petals:
- (1) *Texture.*—Thick.
- (2) *Appearance.*—Inside — velvety; outside — satiny.
- (3) *Form.*—Ovoid to pointed at tip.
- (4) *Arrangement.*—Symmetrically arrange in a circular outline.
- (5) *Petaloids in center.*—Few.

(6) *Persistence.*—Drop off clean.
(7) *Fragrance.*—Strong damask.
(8) *Lasting quality.*—Good on plant and as cut flower.

REPRODUCTIVE ORGANS

A. Stamens, anthers: Medium size, many arranged around styles.
(1) *Color.*—Light yellow 12C.
B. Pollen:
*Color.*—16C.
C. Styles: Uniform; even length.
D. Stigmas:
*Color.*—Orange yellow — 15A.
E. Hips: Large, rounded, RHS 26A when ripe.

PLANT

A. Form: Climber.
B. Growth: Very vigorous and upright.
*Height attained.*—8 to 10 ft. high.
C. Foliage: Compound of 5 to 7 leaflets.
(1) *Size.*—Large.
(2) *Quantity.*—Abundant.
(3) *Color.*—New foliage: Upper side — 137A, with leathery glossy foliage with strong purple overcast; underside — dull near 147C. Old foliage: upper side — RHS 135A-B without so much purple coloring; underside — 147C.
(4) *Shape.*—Pointed.
(5) *Texture.*—Upper side — Leathery with glossy finish. Underside — rough.

(6) *Edge.*—Almost smooth.
(7) *Serration.*—Very small on tip.
(8) *Leaf stem.*—Color — RHS 139C with bronze cast; underside — 139D.
(9) *Stipules.*—Thin and pointed; no bearding.
D. Wood
(1) *New wood.*—Color — 183D with green undercast. Bark — smooth.
(2) *Old wood.*—Color — 137B with purple cast of 183D. Bark — smooth.
E. Thorns:
(1) *Thorns.*—Quantity: On main stalks from base — ordinary; on laterals from stalk — Many. Form: Flat base curved downwards. Length: Medium. Color when young — 178C. Position: Regular.
(2) *Prickles.*—Quantity: On main stalks — few; On laterals — none.
F. Plant's disease resistance:
*Mildew.*—Very good.
*Blackspot.*—Very good.
*Rust.*—None observed.
G. Winter hardiness: Good.

I claim:

1. A new and distinct variety of rose plant of the climbing hybrid tea class, substantially as herein shown and described, characterized particularly as to novelty by its general similarity to its parent variety, "Blue Moon", but different therefrom by its pronounced climbing growth habit.

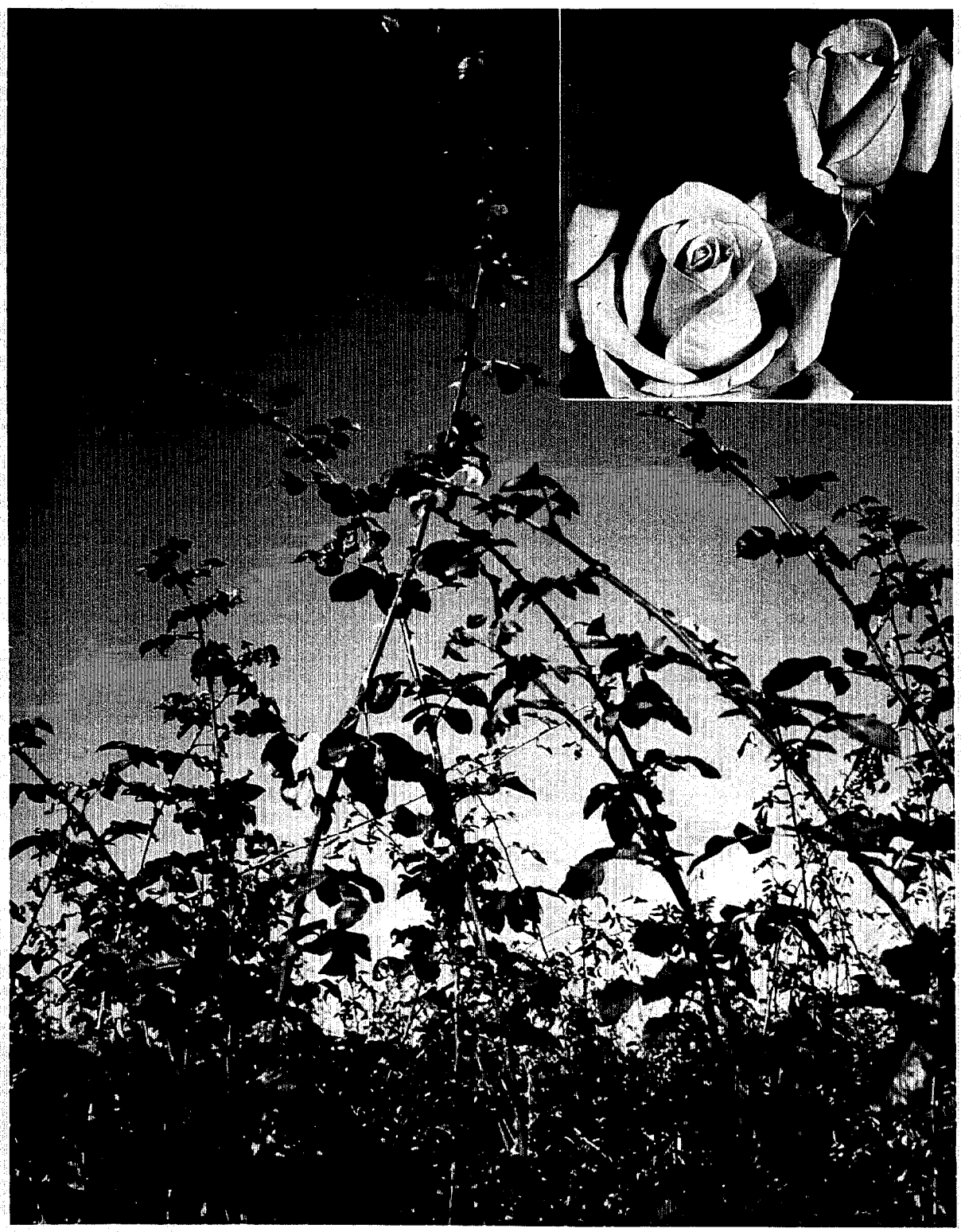

* * * * *